United States Patent
Murahashi et al.

(12)

(10) Patent No.: US 6,193,993 B1
(45) Date of Patent: Feb. 27, 2001

(54) SUPPOSITORY CONTAINING AN ANTIDEMENTIA MEDICAMENT

(75) Inventors: Naokazu Murahashi; Akira Kato; Yukiko Sugaya, all of Ibaraki; Hidenobu Ando, Gunma, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/260,614

(22) Filed: Mar. 2, 1999

(30) Foreign Application Priority Data

Mar. 3, 1998 (JP) .................................................. 10-050567

(51) Int. Cl.⁷ .............................. A61F 9/02; A61F 13/00; A61K 31/445
(52) U.S. Cl. .......................... 424/436; 424/449; 514/319
(58) Field of Search ............................. 514/319; 424/436, 424/449

(56) References Cited

U.S. PATENT DOCUMENTS 5,204,340 * 4/1993 Flaugh et al. ......................... 514/210
5,232,947 * 8/1993 Sato et al. ............................. 514/549
5,364,629 * 11/1994 Kochinke et al. .................... 424/449
5,700,480 * 12/1997 Hille et al. ............................ 424/448

OTHER PUBLICATIONS

Moriearty, Chemical Abstracts, vol. 124, abstract No. 105259, 1995.*

Derwent Abstract of Japanese Patent JP52064418A, May, 1977.*

Derwent Abstract of Japanese Patent JP04257589A, Sep. 1992.*

* cited by examiner

*Primary Examiner*—William R. A. Jarvis
(74) *Attorney, Agent, or Firm*—Birch, Stewart, Kolasch & Birch, LLP

(57) ABSTRACT

The present invention provides a rectum applicable preparation containing an antidementia medicament, wherein the antidementia medicament is incorporated a triglyceride of a fatty acid and/or a water-soluble macromolecule.

11 Claims, 4 Drawing Sheets

Change of the concentration of donepezil in plasma after administration thereof into the rectum of a rat

SUPPOSITORY CONTAINING AN ANTIDEMENTIA MEDICAMENT

FIELD OF THE INVENTION

The present invention relates to a percutaneously applicable preparation containing an antidementia medicament, a percutaneous absorption promoter for an antidementia medicament, or a rectum applicable preparation.

PRIOR ART

Recently, with an increase in old people, sufferers from dementia such as Alzheimer's disease have been increasing. Care thereof and the like have been put into social problems. On the other hand, the development of therapeutic medicaments of dementia has rapidly advanced. For example, donepezil hydrochloride has been widely used as a therapeutic medicament for Alzheimer's disease, from slight to middle degrees, which has acetylcholine esterase inhibiting activity.

Hitherto, in many cases these therapeutic medicaments for dementia have orally been administered in the form of a tablet or the like. As manners for administering a medicament to a patient or the like, there are known percutaneous administration, injection administration, rectum administration and the like, as well as oral administration in the form of a tablet, a capsule, a syrup, a granule, and the like. A suitable manner is selected dependently on the disease thereof and the nature of the medicament.

There may be cases in which it becomes difficult to take an antidementia medicament orally when the condition of dementia gets worse because a dementia patient takes the medicament. Therefore, it is especially useful to administer the medicament percutaneously in the form of an ointment or the like, in the case of a patient whose condition gets worse. However, in general the skin cannot be penetrated by medicaments, and thus it is difficult to cause a sufficiently efficacious amount to be absorbed from the skin into the body. In order to overcome such difficulty, researches have focused on many percutaneous absorption promoters. However, their effects vary dependently on medicaments, and thus it is very difficult to predict percutaneous absorption of a specific medicament from past data.

As an alternative form of administration than oral administration, a rectum applicable preparation can be proposed. The rectum applicable preparation is also called a suppository, and is a preparation that a solid medicament is inserted from the anus to cause the medicament to be absorbed into the rectum. The design for the preparation needs to be conducted considering complex factors such as physical chemistry properties of the medicament, reactivity with a basis, and the like. Thus, it is difficult to produce an optimum rectum applicable preparation by only expansion of the prior art.

DISCLOSURE OF THE INVENTION

The present invention is a percutaneously applicable preparation or a rectum applicable preparation containing an antidementia medicament. The present invention is a percutaneously applicable preparation containing an antidementia medicament, wherein the antidementia medicament is incorporated with a higher alcohol, a lactate of a higher alcohol, an ester of a higher fatty acid and a lower alcohol, or an ester of a fatty acid having 6–18 carbon atoms and propyleneglycol. The present invention is also a percutaneous absorption promoter for an antidementia medicament, which is selected from a higher alcohol, a lactate of a higher alcohol, an ester of a higher fatty acid and a lower alcohol and an ester of a fatty acid having 6–18 carbon atoms and propyleneglycol. Furthermore, the present invention is a rectum applicable preparation containing an antidementia medicament, wherein the antidementia medicament is incorporated with a triglyceride of a fatty acid and/or a water-soluble polymer (macromolecule).

The present invention is a method of promoting a percutaneous absorption of an antidementia medicament, which comprises administering the antidementia medicament to a person suffering from dementia either percutaneously or through the rectum, together with at least one selected from a higher alcohol, a lactate of a higher alcohol, an ester of a higher fatty acid and a lower alcohol, and an ester of a fatty acid having 6–18 carbon atoms and propyleneglycol, and use of an antidementia for manufacturing the preparation as defined above.

DETAILED DESCRIPTION OF THE INVENTION

The antidementia medicament in the present invention means prophylactic agents or preventives and therapeutic agents or remedies for dementia such as cerebrovasular dementia and Alzheimer's disease. Specific example thereof can include donepezil, TAK-147, CP118954 revastigmine, metrifonate, galanthamine and the like. Donepezil is generally used in the form of donepezil hydrochloride, as a therapeutic agent for Alzheimer's disease from slight to middle degrees. Chemical name thereof is 1-benzyl-4-(5,6-dimethoxyindanone-2-yl)methylpyperidine. Chemical names of TAK-147 and CP118954 are 3-[1-(phenylmethyl)pyperidine-4-yl]-1-(2,3,4,5-tetrahydro-1H-1-benzazepine-8-yl)-1-propane fumarate, and 5,7-dihydro-3-[2-[1-(phenylmethyl)-4-pyperidinyl]ethyl]-6H-pyrrolo[4,5-f]-1,2-benzisoxazole-6-onemaleate, respectively. The structural formulae of these compounds are as follows.

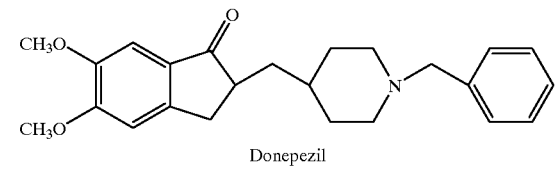
Donepezil

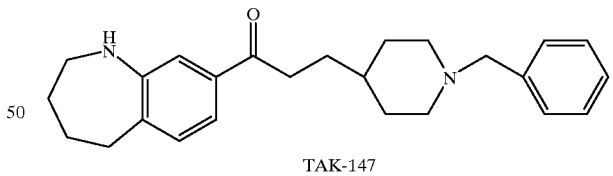
TAK-147

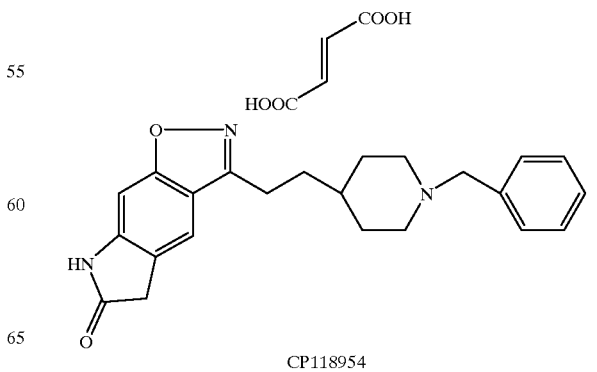
CP118954

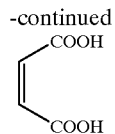

A higher alcohol in the present invention means a straight chain or branched, saturated or unsaturated alcohol having 10 or more carbon atoms, and can include, for example, decanol, lauryl alcohol, myristyl alcohol, cetyl alcohol, stearyl alcohol and the like. Moreover, a lactate of a higher alcohol in the present invention is an ester of the above-mentioned higher alcohol and lactic acid, and can include, for example, myristyl lactate, cetyl lactate, lauryl lactate and the like. The ester of a higher fatty acid and a lower alcohol means an ester of a straight chain or branched, saturated or unsaturated fatty acid having 12 or more carbon atoms and a lower alcohol having 3 or less carbon atoms, and can include, for example, diisopropyl adipate, diethyl sebacate, isopropyl myristate, isopropyl palmitate, and the like. Specific examples of esters of a fatty acid having 6–18 carbon atoms and propyleneglycol in the present invention can include propyleneglycol monocaprylate, propyleneglycol monocaproate, propyleneglycol dicaprylate, and the like. It is available as Cefzol (trade name).

Concerning the mixing ratio of the antidementia medicament to such a substance in the present invention, the substance is in an amount of generally 0.1–10 parts by weight, preferably 0.2–5 parts by weight, and more preferably 0.5–3 parts by weight per part by weight of the antidementia medicament.

The dosage form of the percutaneously applicable preparation according to the present invention is not especially limited, if the dosage form makes application to the skin possible. Examples of the dosage form can include an ointment preparation, a creamy preparation, an adhesive preparation, a lotion preparation, and the like.

In order to prepare these dosage forms, any basis material which is generally used can be used. Examples of an oily basis material can include white Vaseline, purified lanoline, squalane, silicone, fluid paraffin, plant oil, waxes and the like. An aqueous basis material may be water, a lower alcohol, a polyhydric alcohol, a water-soluble macromolecule and the like. The adhesive preparation may be a basis material usually used, examples of which can include, as polymer compositions, ones having adhesiveness such as natural rubber, synthetic rubbers, styrene/isoprene/styrene block copolymers, polyacrylate resins, polyisobutylene resins; and soft polyamide resins, polyvinyl alcohols, polyacrylic resins, and the like. Furthermore, a surfactant, a stabilizer, a preservative or the like may be appropriately incorporated, if necessary. In a conventionally used manner, a percutaneously applicable preparation such as an ointment preparation or an adhesive preparation can be produced. The percentage of the medicament in these percutaneously applicable preparations is usually from 0.1 to 5%.

On the other hand, in the case that the present invention is a rectum applicable preparation, it can be produced by dispersing the medicament into an oily basis such as cacao oil or triglyceride of a fatty acid having from a middle chain to a long chain, or a hydrophilic basis such as macrogol, or the like, in a heating and melting manner or the like. The ratio of the antidementia medicament to the basis is not especially limited. However, the weight of a suppository is usually from 1 to 3 g, and the medicament is contained in an amount of from 0.5 to 50 mg. In general, a rectum applicable preparation is also called a suppository, and according to the form thereof, it can also be administrated into the vagina.

The present invention makes it possible to achieve body circulation of an antidementia medicament that is hardly absorbed from the skin by percutaneous administration thereof, and has an especially great advantage for dementia patients who have difficulty in taking any medicament. It is also a preparation which is excellent in safety since administration can be immediately stopped in the case that an undesired effect is revealed. On the other hand, it is said that in the case of a rectum applicable preparation an absorption rate generally becomes lower than that in the case of oral administration. In spite of it, the rectum applicable preparation has exhibited an increased absorption several times as much as the absorption in the case of oral administration, according to a basis.

Next, the effect of the present invention was confirmed by the following method.

An HWY/Slc male rat (hairless rat) having a body weight of about 300 g (9–10 weekly ages) was put under an anesthetic. After it was checked that its skin had no injuries, the whole of the abdominal skin was stripped off. This was cut into suitable sizes, and then the cut pieces were set to a perpendicular type, in-vitro, diffusing cell having a transmission area of 0.785 cm$^2$. At a receiver side, 3 ml of a pH 7.4 phosphoric acid buffer solution were used. At the donor side, a sample solution described in the following was respectively injected in an amount of 3 ml. Stirring was conducted with stirrers at both sides of the receiver and donor. 200 μl of solutions from the solution at the receptor side were respectively sampled at intervals to determine the quantity of donepezil. The determination of the quantity was performed by high-speed liquid chromatography using an ODS column.

PREPARATION OF THE SAMPLE SOLUTION

Figure 1:
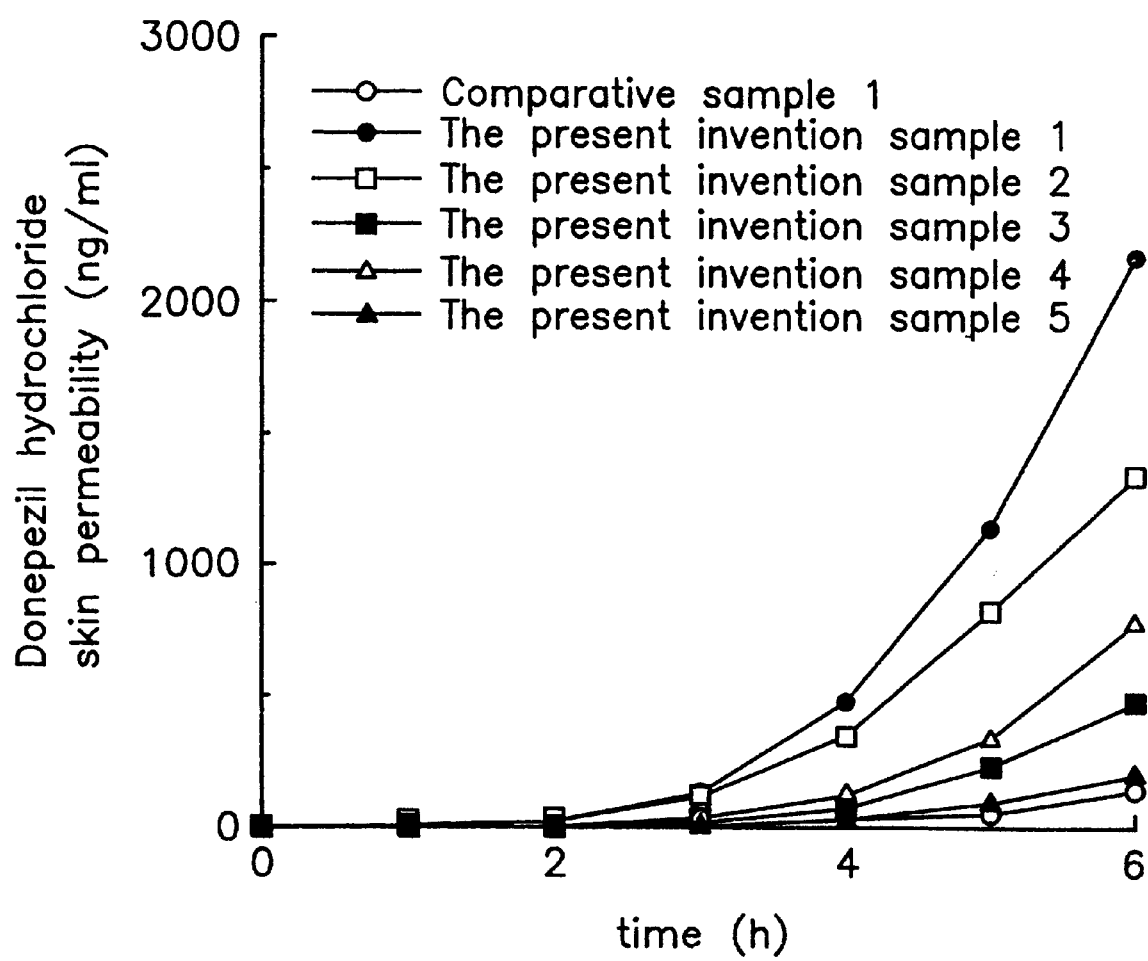
FIG. 1 is a graph showing an effect that an ester of a higher fatty acid and a lower alcohol, or an ester of a fatty acid having 6–18 carbon atoms and propyleneglycol has on skin permeability of the medicament.

To 90 ml of propyleneglycol were added 5 ml of purified water, and then 5 g of donepezil hydrochloride were added to the mixture and stirred. To this suspension was added dropwise 4N NaOH, and then pH of the mixture was adjusted to pH 7. Next, distilled water was added to the mixture so that the total volume would be 100 ml. Thus, a donepezil hydrochloride/propyleneglycol solution (referred to as solution A, hereinafter) was prepared.

Comparative sample 1: 2 ml of propyleneglycol were added to 8 ml of the solution A to prepare a sample.

The present invention sample 1: 1.7 ml of propyleneglycol and 0.3 ml of propyleneglycol monocaprylate (Trade name: Cefzol 218) were added to 8 ml of the solution A to prepare a sample.

The present invention sample 2: 1.7 ml of propyleneglycol and 0.3 ml of diisopropyl adipate were added to 8 ml of the solution A to prepare a sample.

The present invention sample 3: 1.7 ml of propyleneglycol and 0.3 ml of isopropyl myristate were added to 8 ml of the solution A to prepare a sample.

The present invention sample 4: 1.7 ml of propyleneglycol and 0.3 ml of diethyl sebacate were added to 8 ml of the solution A to prepare a sample.
The present invention sample 5: 1.7 ml of propyleneglycol and 0.3 ml of isopropyl palmitate were added to 8 ml of the solution A to prepare a sample.
The present invention sample 6: 1.7 ml of propyleneglycol and 0. 3 ml of decanol were added to 8 ml of the solution A to prepare a sample.
The present invention sample 7: 1.7 ml of propyleneglycol and 0.3 ml of lauryl alcohol were added to 8 ml of the solution A to prepare a sample.
The present invention sample 8: 1.7 ml of propyleneglycol and 0.3 ml of myristyl alcohol were added to 8 ml of the solution A to prepare a sample.
The present invention sample 9: 1.7 ml of propyleneglycol and 0.3 ml of melted cetyl alcohol were added to 8 ml of the solution A to prepare a sample.
The present invention sample 10: 1.7 ml of propyleneglycol and 0.3 ml of stearyl alcohol were added to 8 ml of the solution A to prepare a sample.
The present invention sample 11: 1.7 ml of propyleneglycol and 0.3 ml of melted myristyl lactate were added to 8 ml of the solution A to prepare a sample.
The present invention sample 12: 1.7 ml of propyleneglycol and 0.3 ml of cetyl lactate were added to 8 ml of the solution A to prepare a sample.

Figure 2:
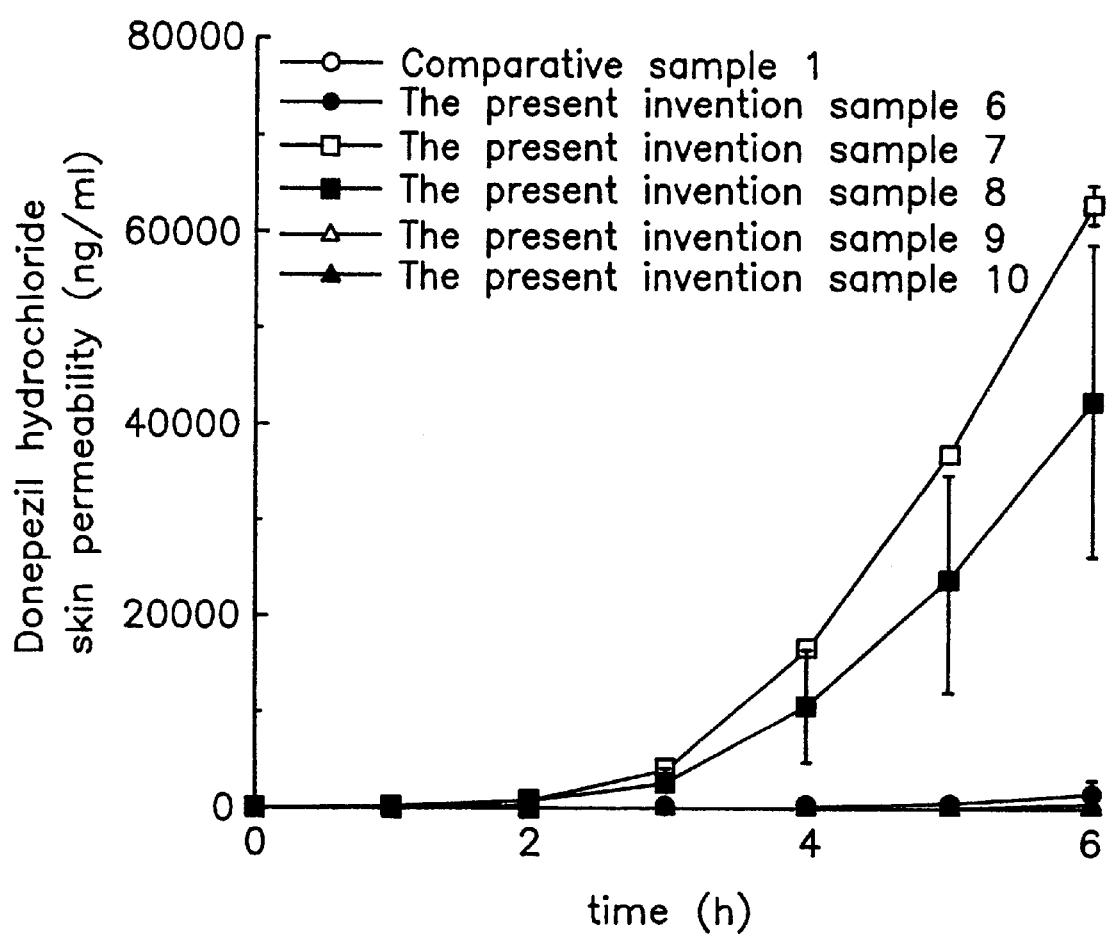
FIG. 2 is a graph showing an effect that a higher alcohol has on skin permeability of the medicament.
Figure 3:
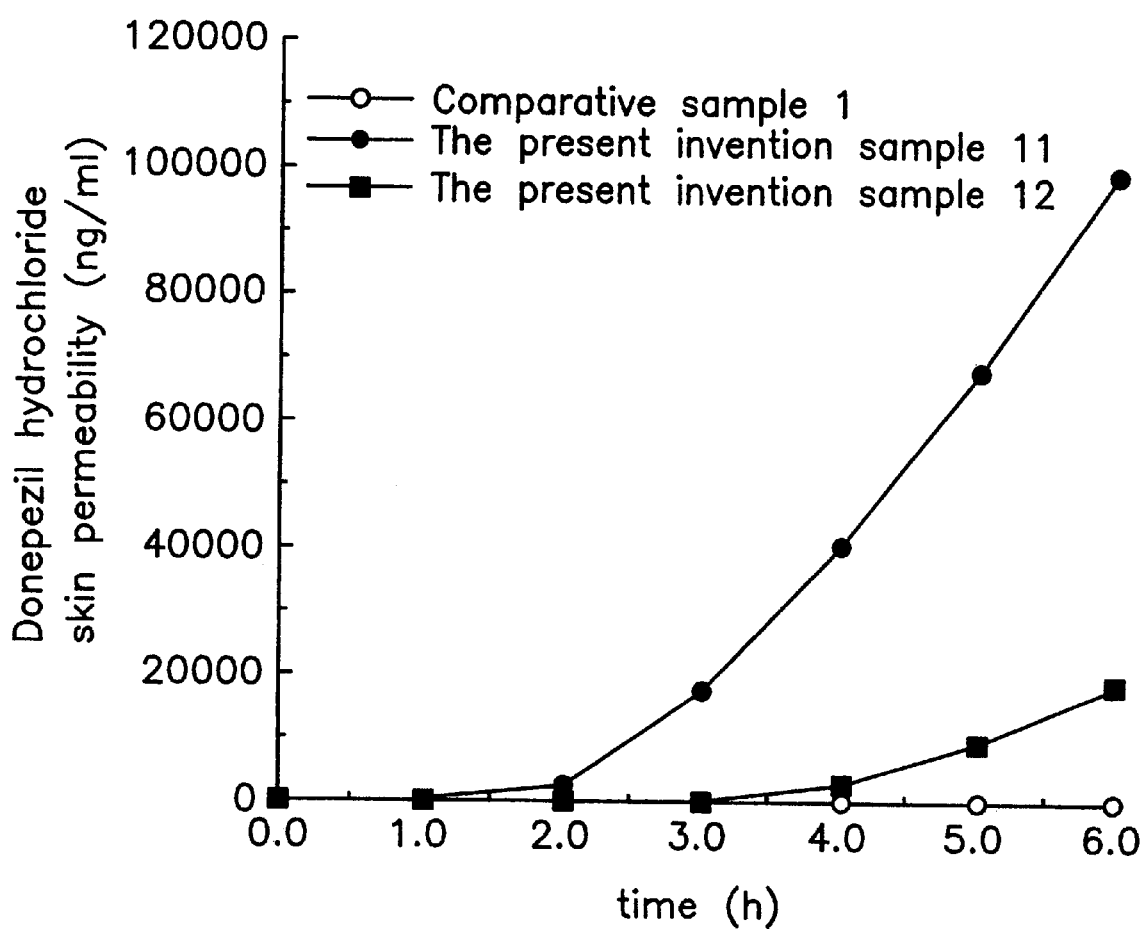
FIG. 3 is a graph showing an effect that an ester lactate of a higher alcohol has on skin permeability of the medicament.

The results are shown in FIGS. 1 to 3.

From the figures, it is evident that the percutaneously applicable preparation according to the present invention causes the skin permeability of the medicament to remarkably increase.

On the other hand, in the case of a rectum applicable preparation, the following samples were inserted into the rectum of a rat that fasted for 24 hours in an amount of 500 mg per kg of the body, and then blood was sampled at intervals. The concentration of the medicament was determined by high-speed chromatography to obtain an absorption rate from the ratio to that by intravenous injection.

The present invention sample 13: 60 mg of donepezil hydrochloride were added to 15 g of Wittepzol H and dissolved therein, and then the solution was cooled to prepare a sample.

The present invention sample 14: 60 mg of donepezil hydrochloride were added to 3.5 g of polyethyleneglycol 1500 and 1.5 g of polyethyleneglycol 6000 and dissolved therein, and then the solution was cooled to prepare a sample.

Figure 4:
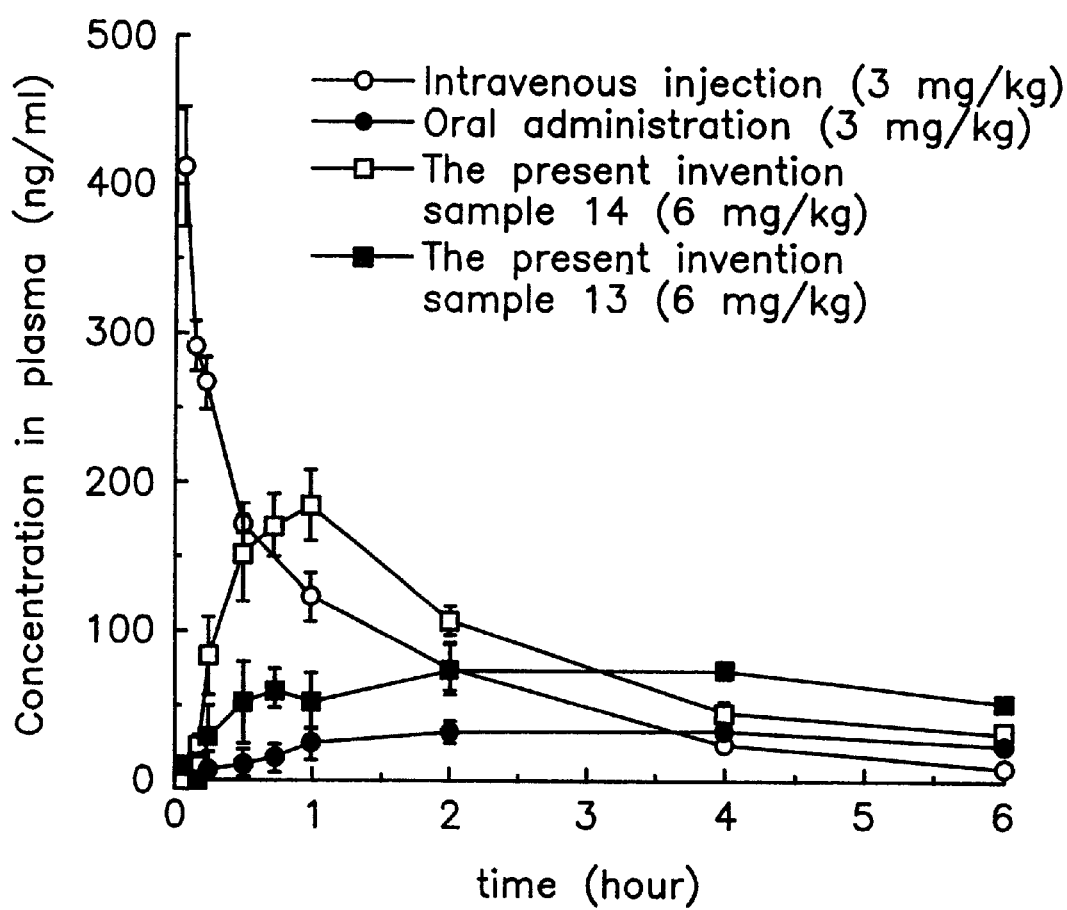
FIG. 4 is a graph showing the absorption of a suppository.

The results are shown in FIG. 4.

EXAMPLES

The following will describe the present invention in detail referring to Examples, but the present invention is not limited to these Examples.

Example 1

Propyleneglycol was heated to 60° C. and then donepezil hydrochloride was added thereto and dispersed and dissolved therein. To the mixture, was added a mixture of cetyl lactate and Plastibase (tradename) which were beforehand heated to 60° C. The mixture was cooled to room temperature while being stirred, so as to obtain an oily ointment preparation having the following composition.

| Donepezil hydrochloride | 5% by weight |
| Cetyl lactate | 10 |
| Propyleneglycol | 15 |
| Plastibase | 70 |

Example 2

Donepezil hydrochloride was added to myristyl lactate and dispersed therein. On the other hand, sorbitantrioleate and white Vaseline were heated to 60° C. and then were uniformly mixed. To this, the above-mentioned stirred homogenous product of myristyl lactate and donepezil hydrochloride was added. The whole amount thereof was homogeneously stirred and mixed, and then was cooled to room temperature, so as to obtain an oily ointment having the following composition.

| Donepezil hydrochloride | 1.5% by weight |
| Myristyl lactate | 5% by weight |
| Sorbitantrioleate | 3% by weight |
| White Vaseline | 90.5% by weight |

Example 3

Lauryl alcohol, polyoxyethylene (20) sorbitan monooleate, the Japanese Pharmacopoeia macrogol ointment and a preservative were heated to 60° C. and then were homogeneously mixed. Thereafter, donepezil hydrochloride was added to the mixture and then the resultant mixture was sufficiently mixed while being cooled, so as to obtain a hydrophilic ointment having the following composition.

| Donepezil hydrochloride | 2% by weight |
| Lauryl alcohol | 3% by weight |
| Polyoxyethylene (20) sorbitan monooleate | 2% by weight |
| The Japanese Pharmacopoeia macrogol ointment | 92.9% by weight |
| Preservative (methylparaben) | 0.1% by weight |

Example 4

Squalane, isopropyl myristate, stearic acid, monoglyceride stearate, sorbitan monopalmitate, polyoxyethylene (20) sorbitan monostearate and myristyl lactate were heated to 70° C. and then were homogeneously dissolved. Donepezil hydrochloride was added to the mixture and then the resultant mixture was stirred to be homogenous. To the mixture were gradually added propyleneglycol, a preservative agent and purified water that were separately heated to 60° C. The resultant mixture was cooled to about 30° C. while being stirred, so as to obtain an O/W type creamy preparation having the following composition.

| Donepezil hydrochloride | 2% by weight |
| Squalane | 8% by weight |
| Isopropyl myristate | 4% by weight |
| Stearic acid | 4% by weight |
| Monoglyceride stearate | 4% by weight |

-continued

| | |
|---|---|
| Sorbitan palmitate | 1.5% by weight |
| polyoxyethylene (20) sorbitan monostearate | 0.5% by weight |
| Myristyl lactate | 5% by weight |
| Propyleneglycol | 5% by weight |
| Preservative (methylparaben) | 0.1% by weight |

Example 5

Wittepzol H15 was heated to 50° C. and then donepezil hydrochloride was added thereto, and dispersed and dissolved therein. The solution was poured into a container for a suppository, and then was gradually cooled to room temperature to obtain an oily suppository having the following composition.

| | |
|---|---|
| Donepezil hydrochloride | 1% by weight |
| Wittepzol H15 | 99% by weight |

Example 6

Polyethyleneglycol 1500 and polyethyleneglycol 6000 were heated to 60° C. and then donepezil hydrochloride was added to the mixture, and dispersed and dissolved therein. The solution was poured into a container for a suppository, and then was gradually cooled to room temperature to obtain a hydrophilic suppository having the following composition.

| | |
|---|---|
| Donepezil hydrochloride | 1% by weight |
| Polyethyleneglycol 1500 | 69% by weight |
| Polyethyleneglycol 6000 | 30% by weight |

What is claimed is:

1. A rectum applicable preparation comprising an antidementia medicament, which comprises at least one selected from the group consisting of a higher alcohol, a lactate of a higher alcohol, an ester of a higher fatty acid and a lower alcohol and an ester of a fatty acid having 6–18 carbon atoms and propyleneglycol, provided that the ester of the higher fatty acid and the lower alcohol is not isopropyl myristate.

2. The preparation as claimed in claim 1, wherein the higher alcohol is a straight chain or branched, saturated or unsaturated alcohol having 10 or more carbon atoms.

3. The preparation as claimed in claim 1, wherein the higher alcohol is at least one selected from the group consisting of decanol, lauryl alcohol, myristyl alcohol, cetyl alcohol and stearyl alcohol.

4. The preparation as claimed in claim 1, wherein the lactate of the higher alcohol is at least one selected from the group consisting of myristyl lactate, cetyl lactate and lauryl lactate.

5. The preparation as claimed in claim 1, wherein the ester of the higher fatty acid and the lower alcohol is at least one selected from the group consisting of diisopropyl adipate, diethyl sebacate, and isopropyl palmitate.

6. The preparation as claimed in claim 1, wherein the ester of the fatty acid having 6–18 carbon atoms and propyleneglycol is at least one selected from the group consisting of propyleneglycol monocaprylate, propyleneglycol monocaproate and propyleneglycol dicaprylate.

7. The rectum applicable preparation as claimed in claim 1, wherein the antidementia medicament is donepezil hydrochloride.

8. A method of promoting a rectal absorption of an antidementia medicament, which comprises administering the antidementia medicament to a person suffering from dementia through the rectum, together with at least one selected from a higher alcohol, a lactate of a higher alcohol, an ester of a higher fatty acid and a lower alcohol and an ester of a fatty acid having 6–18 carbon atoms and propyleneglycol, provided that the ester of the higher fatty acid and the lower alcohol is not isopropyl myristate.

9. The rectum applicable preparation as claimed in claim 1, which further comprises at least one selected from the group consisting of a triglyceride of a fatty acid and a water-soluble polymer.

10. A method for treating dementia comprising administering an effective amount of the preparation as defined in claim 1 to a person suffering from dementia.

11. A method for treating dementia as claimed in claim 10 wherein said preparation is administered rectally.

* * * * *